US011244756B1

(12) United States Patent
West et al.

(10) Patent No.: US 11,244,756 B1
(45) Date of Patent: Feb. 8, 2022

(54) INTEGRATED SYSTEM AND METHOD FOR RECEIVING AND PROCESSING REAL-TIME DIGITAL DATA CONCERNING TRANSPORTATION AND SERVICE MONITORING SCHEDULING

(71) Applicant: TeleTracking Technologies, Inc., Pittsburgh, PA (US)

(72) Inventors: Brian West, Pittsburgh, PA (US); Thomas Perry, Pittsburgh, PA (US); Joseph C. Schuck, Pittsburgh, PA (US); Steven Gaghan, Pittsburgh, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 474 days.

(21) Appl. No.: 16/167,192

(22) Filed: Oct. 22, 2018

Related U.S. Application Data

(60) Provisional application No. 62/575,341, filed on Oct. 20, 2017.

(51) Int. Cl.
  *G16H 40/20* (2018.01)
  *G16H 10/60* (2018.01)
  *G16H 80/00* (2018.01)
(52) U.S. Cl.
  CPC ............ *G16H 40/20* (2018.01); *G16H 10/60* (2018.01); *G16H 80/00* (2018.01)
(58) Field of Classification Search
  None
  See application file for complete search history.

(56) References Cited

U.S. PATENT DOCUMENTS

| 10,832,579 | B2* | 11/2020 | Patel | G08G 1/202 |
| 2005/0038696 | A1* | 2/2005 | Kalevik | G16H 40/67 705/13 |
| 2011/0313804 | A1* | 12/2011 | Camp | G06Q 30/0284 705/7.13 |
| 2012/0041675 | A1* | 2/2012 | Juliver | G06Q 30/0283 701/465 |
| 2013/0218647 | A1* | 8/2013 | Kroll | G07B 15/02 705/13 |
| 2013/0246301 | A1* | 9/2013 | Radhakrishnan | G06Q 30/0282 705/347 |

(Continued)

*Primary Examiner* — Jonathan Ng
(74) *Attorney, Agent, or Firm* — Ference & Associates LLC

(57) ABSTRACT

Computer implemented systems and methods are provided for requesting and monitoring optimal patient transport. In embodiments, a system for monitoring optimal patient transport may comprise at least one processor configured to receive transfer request data from an initial user for a patient and determine relevant patient and relevant patient data based on the transfer request data. The at least one processor may be configured to transmit a transfer request to one or more transport providers, receive and store one or more transportation quotes from one or more transport providers through a bid process that is set for a specific time interval, and analyze received one or more transportation quote with previously stored transportation quotes. The at least one processor may further determine winning transport provider and pending transport data, and generate instructions to display a user interface depicting a first representation of a pending transport at a first time.

20 Claims, 9 Drawing Sheets

(56) References Cited

U.S. PATENT DOCUMENTS

2014/0229258 A1* 8/2014 Seriani ............ G06Q 10/08345
705/14.23
2015/0066557 A1* 3/2015 Lichti ...................... G08G 1/20
705/7.15

* cited by examiner

11,244,756 B1

INTEGRATED SYSTEM AND METHOD FOR RECEIVING AND PROCESSING REAL-TIME DIGITAL DATA CONCERNING TRANSPORTATION AND SERVICE MONITORING SCHEDULING

CROSS-REFERENCE TO RELATED APPLICATIONS

This application claims priority to U.S. Provisional Application No. 62/575,341, filed on Oct. 20, 2017, the entirety of which is incorporated by reference in its entirety.

TECHNICAL FIELD

The present disclosure relates generally to the field of real-time transmission of digital data. More particularly, disclosed embodiments may be directed to receiving, processing, and transmitting digital data over a plurality of channels, such as data concerning transportation and service monitoring scheduling.

BACKGROUND

Improvements in modern medicine in recent decades have resulted in many benefits, including earlier diagnosis of medical conditions, more effective preventative measures, and new enhanced treatment methods. However, there are still many auxiliary aspects of delivering effective medical care that have progressed more slowly, preventing medical care systems from operating at an optimal level. One such aspects includes patient transportation, which, at the moment, requires medical care providers to coordinate with multiple entities through numerous communications to ensure acceptable transportation. For example, using current systems, medical personnel have to manually reach out to multiple medical transportation providers to schedule transportation. Additionally, personnel may need to contact providers to determine the status of a scheduled transport.

SUMMARY

Disclosed embodiments relate to computerized systems and methods for requesting and monitoring optimal patient transport. Consistent with the present embodiments, a system is disclosed. The system may include at least one processor in communication with a communications network and a storage medium. The at least one processor may be configured to execute instructions stored in the storage medium comprising instructions that, when executed, configure the at least one processor to request and monitor patient transport to other facilities in an optimal and resource-efficient manner. The at least one processor may be configured to execute the instructions to receive transfer request data from an initial user for a patient, determine relevant patient and relevant patient data based on the transfer request data, transmit a transfer request to one or more transport providers, receive and store one or more transportation quotes from one or more transport providers through a bid process that is set for a specific time interval, analyze received one or more transportation quote with previously stored transportation quotes, determine winning transport provider and pending transport data based on the one or more transportation quotes received, generate, based on the pending transport data, instructions to display a user interface depicting a first representation of a pending transport at a first time, receive real-time and historical data associated with a facility and the pending transport, and generate, based on the real-time and historical, instructions to display a user interface depicting a second representation of progress of the pending transport at a second time.

Consistent with the present embodiments, a method for requesting and monitoring optimal patient transport is disclosed. The method may comprise receiving, by at least one processor in communication with a communications network, transfer request data from an initial user for a transferee, determining relevant transferee and relevant transferee data based on the transfer request data, transmitting a transfer request to one or more transport providers, receiving and storing one or more transportation quotes from one or more transport providers through a bid process that is set for a specific time interval, analyzing received one or more transportation quote with previously stored transportation quotes; determining winning transport provider and pending transport data based on the one or more transportation quotes received, generating, based on the pending transport data, instructions to display a user interface depicting a first representation of a pending transport at a first time, receiving real-time and historical data associated with a facility and the pending transport, and generating, based on the real-time and historical, instructions to display a user interface depicting a second representation of progress of the pending transport at a second time.

Consistent with other disclosed embodiments, non-transitory computer-readable storage media may store program instructions, which are executed by one or more processors to perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments and, together with the description, serve to explain the disclosed principles. In the drawings.

DETAILED DESCRIPTION OF EXEMPLARY EMBODIMENTS

Reference will now be made in detail to exemplary embodiments, examples of which are illustrated in the accompanying drawing and disclosed herein. Wherever convenient, the same reference numbers will be used throughout the drawings to refer to the same or like parts.

This fragmented process is highly inefficient and consumes significant amounts of valuable time and resources.

For example, using current systems, medical personnel have to manually reach out to multiple medical transportation providers, resulting in inefficient communication methods and often selecting suboptimal medical transportation providers. Not only does the manual labor require medical personnel to waste precious time that could otherwise be used for direct patient care, but it also typically results in patients occupying rooms or patient beds for longer periods of time than needed. For example, a patient may be approved for discharge in the morning, but the selected transportation provider may not arrive until the evening because the medical personnel in charge of acquiring transportation was not able to find the optimal transportation provider, but merely chose the first available one that is capable of meeting any requirements set forth. It is likely that, in that scenario, another transportation provider had morning availability, which would have allowed the discharged patient to be efficiently transported, creating an open bed or room for another patient to occupy.

Furthermore, medical personal also lack the ability to easily track the status of any given transportation reservation. They have to rely on arduous manual methods to obtain a status update from a transportation provider. Again, such a process further augments the overall inefficient transportation process, which can be easily derailed by a simple conflict. While vast amounts of real-time and historical data may be available in some hospitals, existing hospitals lack the ability to display large amounts of information quickly and in a way that is easy-to-read for hospital personnel.

Additionally, traditional transportation scheduling techniques also negatively impact the transportation providers, who lack access to readily available information to optimize their resources. For example, a transportation provider usually reacts to a transportation request at the moment the request was made. This may result in resources, such as the vehicles transportation provider's use to transport patients, to be located much farther away than where a transportation request is coming from.

In view of the drawbacks of current systems, improved systems and methods for facilitating patient transportation are needed.

Figure 1:
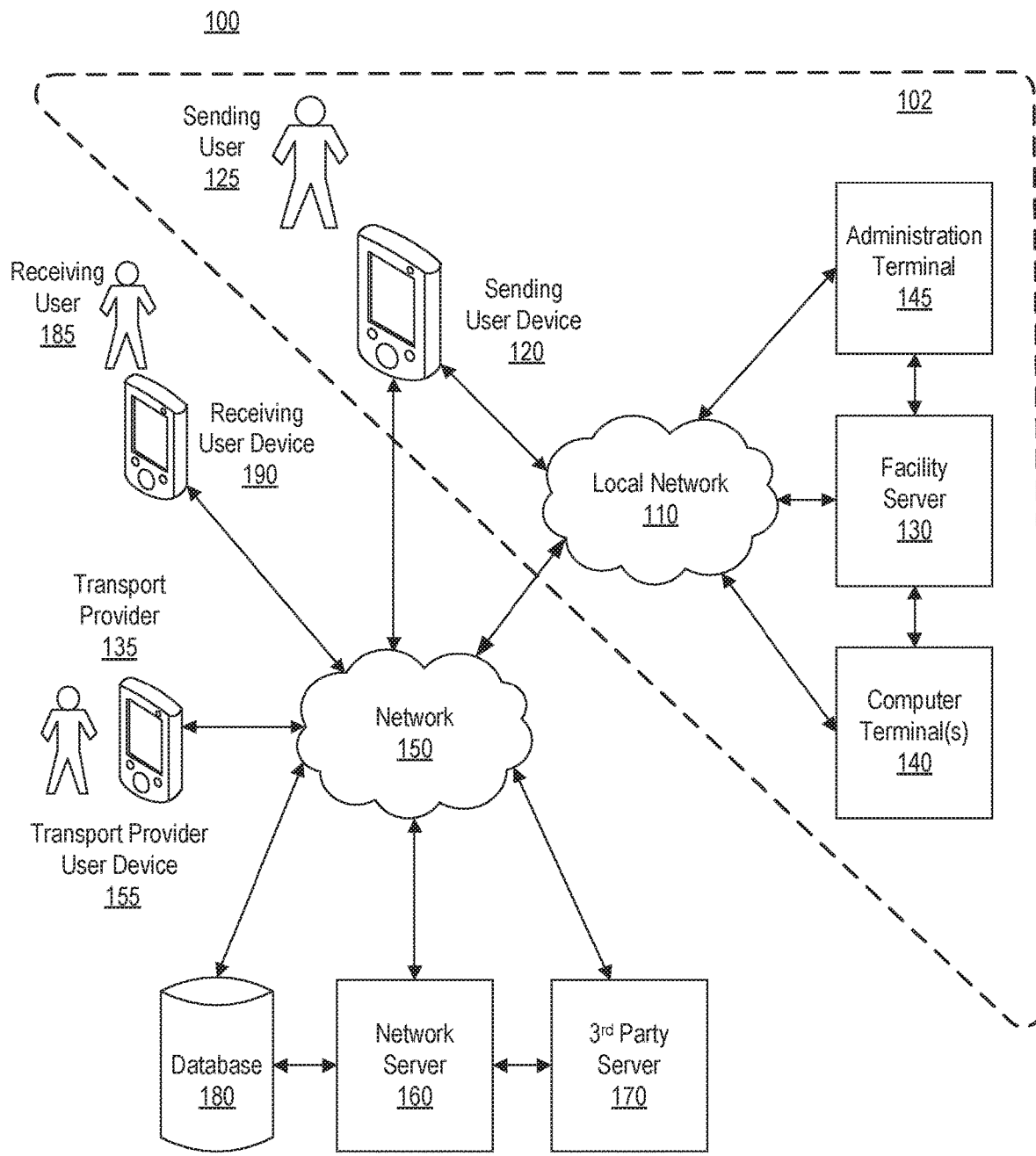
FIG. 1 depicts an example of a system environment for managing medical transportation for patients, consistent with embodiments of the present disclosure.

FIG. 1 shows a diagram of a computer system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, system 100 may include a facility server 130, a computer terminal 140, an administration terminal 145, a sending user device 120, network server 160, third party server 170, and database 180. The components of system 100 may communicate directly, through network 150, through local network 110, or through a combination of communications methods. In some embodiments, local network 110, facility server 130, computer terminal 140, administrator terminal 145, and sending user device 120 may be physically disposed within a facility such as a medical facility such as a hospital or office building (i.e. as facility system 102) while network 150, network server 160, third party server 170, and database 180 may be external to the medical facility. Other components known to one of ordinary skill in the art may be included in system 100 to perform tasks consistent with the disclosed embodiments.

Computer terminal 140 may be a standalone device disposed in an office, a room, an employee station, or an alternative central location in a workplace. In some embodiments, computer terminal 140 may be a desktop or notebook computer, a flat panel or projected display, touch screen monitor, or any other display. In some embodiments, computer terminal 140 may be associated with a particular room in a facility, such as a patient room, hotel room, conference room, or any other type of room. Thus, a message or task request received from a computer terminal 140 may automatically associate the task request or message with the room in which computer terminal 140 is installed.

Administrator terminal 145 may include a computer system or device associated with a sending user 125 that manages or oversees a portion of facility system 102. For example, administrator terminal 145 may comprise a computer system located at a head nurse station, a housekeeping manager's office, or any other department manager's office or station. In some embodiments, administrator terminal 145 may be a computer terminal 145 designated to a particular user or class of users, and may include any of the functions and comprise any of the hardware discussed with respect to computer terminal 145.

Sending user 125 may be an employee in a workplace environment such as a physician, nurse, a technician, supervisor, manager, support personnel, or any other individual involved with the care of a patient, and is located where a patient requires transport from. Sending user 125 may operate computer terminal 140, sending user device 120, and/or another computer (not shown) to interact with system 100. System 100 may include multiple types of users such as, for example, caregivers, technicians, task requestors, transport providers, and medical personnel receiving a new patient. Task requestors may include one or more individuals who initiate a request for a certain task to be completed, such as a nurse requesting approval to discharge a specific patient or initiating a patient transfer request.

Sending user device 120 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, sending user device 120120 may be a computer system or mobile computer device that is operated by sending user 125. In some embodiments, sending user device 120 may be associated with a particular individual such as sending user 125, such that sending user 125 may initiate a transfer request from sending user device 120.

Receiving user 185 may be an employee in a workplace environment such as a physician, nurse, a technician, supervisor, manager, support personnel, or any other individual involved with the care of a patient, and is located where a patient requires transport to. Receiving user device 190 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, receiving user device 190 may be a computer system or mobile computer device that is operated by receiving user 185. In some embodiments, receiving user device 190 may be associated with a particular individual such as receiving user 185, such that data regarding patient transfers to receiving user 185 would be sent to and from receiving user device 190.

Transport provider 135 may be an employee in a workplace environment such as an emergency medical response team member, vehicle driver, nursing home facility member, or any other individual involved with the transportation of a patient. Transport provider user device 155 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, transport provider user device 155 may be a computer system or mobile computer device that is operated by transport provider 135. In some embodiments, transport provider user device 155 may be associated with a particular individual such as transport provider 135, such that data regarding patient transfers to transport provider 135 would be sent to and from transport provider user device 155.

In some embodiments, sending user device 120 may communicate with facility server 130 and/or network server 160 via direct wireless communication links (not shown), or via a combination of one or more of local network 110 and/or network 150.

In some embodiments, one or more individuals such as the receiving user 185 may send and receive information to facility system 102. In the example shown, receiving user 185 may operate receiving user device 190, which may be similar in form and function to sending user device 120. In some embodiments, receiving user 185 may provide information including, but not limited to, hospital status, emergency information, availability to receive a patient, and real-time capacity data.

Facility server 130 may be operated by a facility such as a hospital, business, retail location, and the like. Facility server 130 may enable communication within a computer-based system including computer system components such as desktop computers, workstations, tablets, hand held computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™ Ethernet, and other suitable short-range connections that enable computer terminal 140 and sending user device 120 to send and receive information between the components of system 100. In some embodiments, local network 110 may be excluded, and computer terminal 140 and sending user device 120 may communicate with system 100 components via network 150. In some embodiments, computer terminal 140 and/or sending user device 120 may communicate with one or more system 100 components via a direct wired or wireless connection. In some embodiments, local network 110 may comprise a portion of network 150 or an extension of network 150.

Network server 160, third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with one or more third-party services such as mapping services, data analysis services, or storage services. Alternatively, third party server 170 may be associated with other third party entities such as a medical entity or hospital where the receiving user 185 is located, or a transport provider capable of fulfilling a patient transfer request.

In some embodiments, system 100 may include configurations that vary from the example shown in FIG. 1, which illustrates a facility system 102 working in concert with a cloud computing system including network server 160, third party server 170, and database 180. As a first variation, system 100 may include a facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and interface-related functions of the disclosed embodiments.

Figure 2:
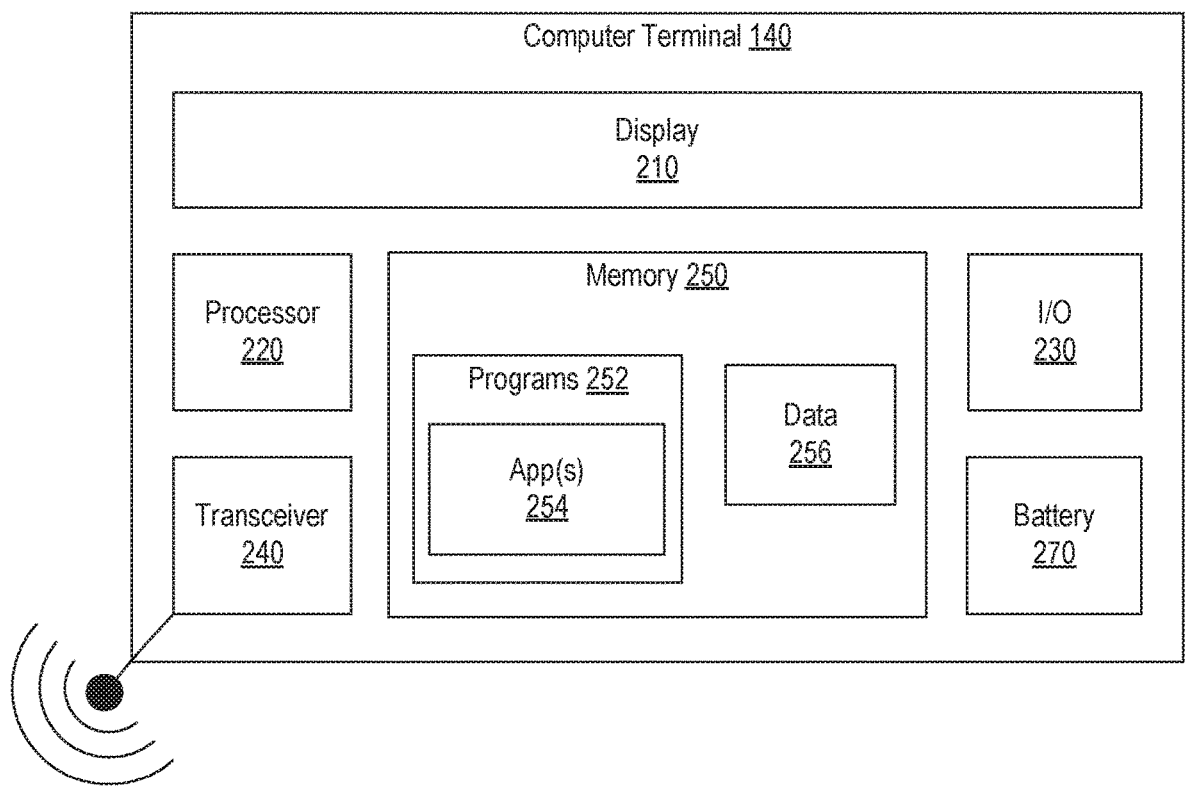
FIG. 2 depicts an example of a computer terminal, consistent with embodiments of the present disclosure.

FIG. 2 shows a diagram of computer terminal 140, consistent with disclosed embodiments. As shown, computer terminal 140 may include a display 210, one or more processors 220, input/output ("I/O") devices 230, a transceiver 240 memory 250, and battery 270.

Display 210 may include one or more screens for displaying task management information such as, for example, liquid crystal display (LCD), plasma, cathode ray tube (CRT), or projected screens.

Processor 220 may be one or more known processing devices, such as microprocessors manufactured by Intel™ or AMD™ or licensed by ARM. Processor 220 may constitute a single core or multiple core processors that executes parallel processes simultaneously. For example, processor 220 may be a single core processor configured with virtual processing technologies. In certain embodiments, processor 220 may use logical processors to simultaneously execute and control multiple processes. Processor 220 may implement virtual machine technologies, or other known technologies to provide the ability to execute, control, run, manipulate, store, etc. multiple software processes, applications, programs, etc. In another embodiment, processor 220 may include a multiple-core processor arrangement (e.g., dual, quad core, etc.) configured to provide parallel processing functionalities to allow computer terminal 140 to execute multiple processes simultaneously. One of ordinary skill in the art would understand that other types of processor arrangements could be implemented that provide for the capabilities disclosed herein.

I/O devices 230 may include one or more devices that allow computer terminal 140 to receive input from a user. I/O devices 230 may include, for example, one or more pointing devices, keyboards, buttons, switches, touchscreen panels, cameras, barcode scanners, radio frequency identification (RFID) tag reader, and/or microphones.

Transceiver 240 may include one or more communication modules for establishing communication between computer terminal 140 and other devices of system 100 via, for example, local network 110 and/or network 150. For example, transceiver 240 may include circuitry and one or more antennas for communicating wirelessly with local network 110 using a short range/near-field wireless communication protocol such as Bluetooth™, Bluetooth™ LE, WiFi, and Zigbee. Further, transceiver 240 may communicate with network 150 and/or local network 110 using any known network protocol including any form of wired or wireless internet access.

Memory 250 may include a volatile or non-volatile, magnetic, semiconductor, solid-state, tape, optical, removable, non-removable, or other type of storage device or tangible (i.e., non-transitory) computer-readable medium that stores one or more program(s) 252, such as app(s) 254, and data 256. Data 256 may include, for example, user information, patient information, facility information, third-party facility information, transportation provider information and display settings and preferences.

Program(s) 252 may include operating systems (not shown) that perform known operating system functions when executed by one or more processors. By way of example, the operating systems may include Microsoft Windows™, Unix™, Linux™ Android™ and Apple™ operating systems, Personal Digital Assistant (PDA) type operating systems, such as Microsoft CE™, or other types of operating systems. Accordingly, disclosed embodiments may operate and function with computer systems running any type of operating system. Computer terminal 140 may also include communication software that, when executed by a processor, provides communications with network 150 and/or local network 110, such as Web browser software, tablet, or smart hand held device networking software, etc.

Program(s) 252 may also include app(s) 254, such as a patient transportation app, which when executed causes computer terminal 140 to perform processes related to processing real-time and historical patient and third-party data, and generating graphical user interfaces based on the data. For example, app(s) 254 may configure computer terminal 140 to generate and display an interface showing information regarding one or more transport providers and pending transfer statuses to provide users such as hospital administrators and other personnel a graphical view of the optimal available transfer providers and the status of any pending patient transfers. In another example, app(s) 254 may configure computer terminal 140 to generate and display an interface showing a transfer request interface allowing a user to submit a patient transportation request. The interfaces may graphically display current and historical facility information such as potential transport provider information, pending transfer request information, estimated transfer pick-up, estimated transfer drop-off, transport provider data, and GPS location data.

Furthermore, app(s) 254 may configure computer terminal 140 to analyze the current and historical information associated with the facility to predict estimated future patient transfer requests and transmit the estimated data in predictive graphical user interfaces to the transport provider user device 155. In some embodiments, app(s) 254 may configure one or more computer systems to analyze historical patient itinerary data and hospital census and performance data to identify patterns, trends or correlative relationships in the historical data. For example, trends in historical data may indicate that certain patient diagnoses are associated with certain lengths of stay, or often experience delays and complications in certain portions of the itinerary, thereby allowing predictive analysis of potential transfers required in the future. Historical data, identified trends and patterns, and correlative relationships may be identified through regression analysis, queuing analysis and other known statistical analysis methods, stored, and recalled to predict future facility utilization and patient discharge or transfer dates, and used to predict patient transportation needs. This predictive analysis data may be presented to the transport providers in an easy-to-read graphical interface to enable transport providers to make more informed decisions based on discharge or transfer date probabilities and to ultimately provide ever-improving patient care and efficiency. Correlations could be stored, retrieved and processed as Stochastic Information Packets (SIPs), Distribution Strings (DIST) or Stochastic Library Unit with Relationships Preserved (SLURPs). As discussed in further detail below, in some embodiments the implementation of these functions and the advantages realized by the present embodiments are attributed to the use of high-speed data and communication network, as well as personal communication and tracking devices disposed throughout a hospital. In some embodiments, system 100 may analyze types of information disclosed herein for an external medical facility such as a post-acute care facility. In such embodiments, system 100 may perform predictive analytics with respect to an external facility, to automatically select an external facility, schedule post-acute care, and schedule transportation for the patient. In some embodiments, system 100 may analyze a patient schedule to identify historical care appointment times, and predict a preferred date and time for future post-acute care appointments based on the analyzed schedule.

Figure 3:
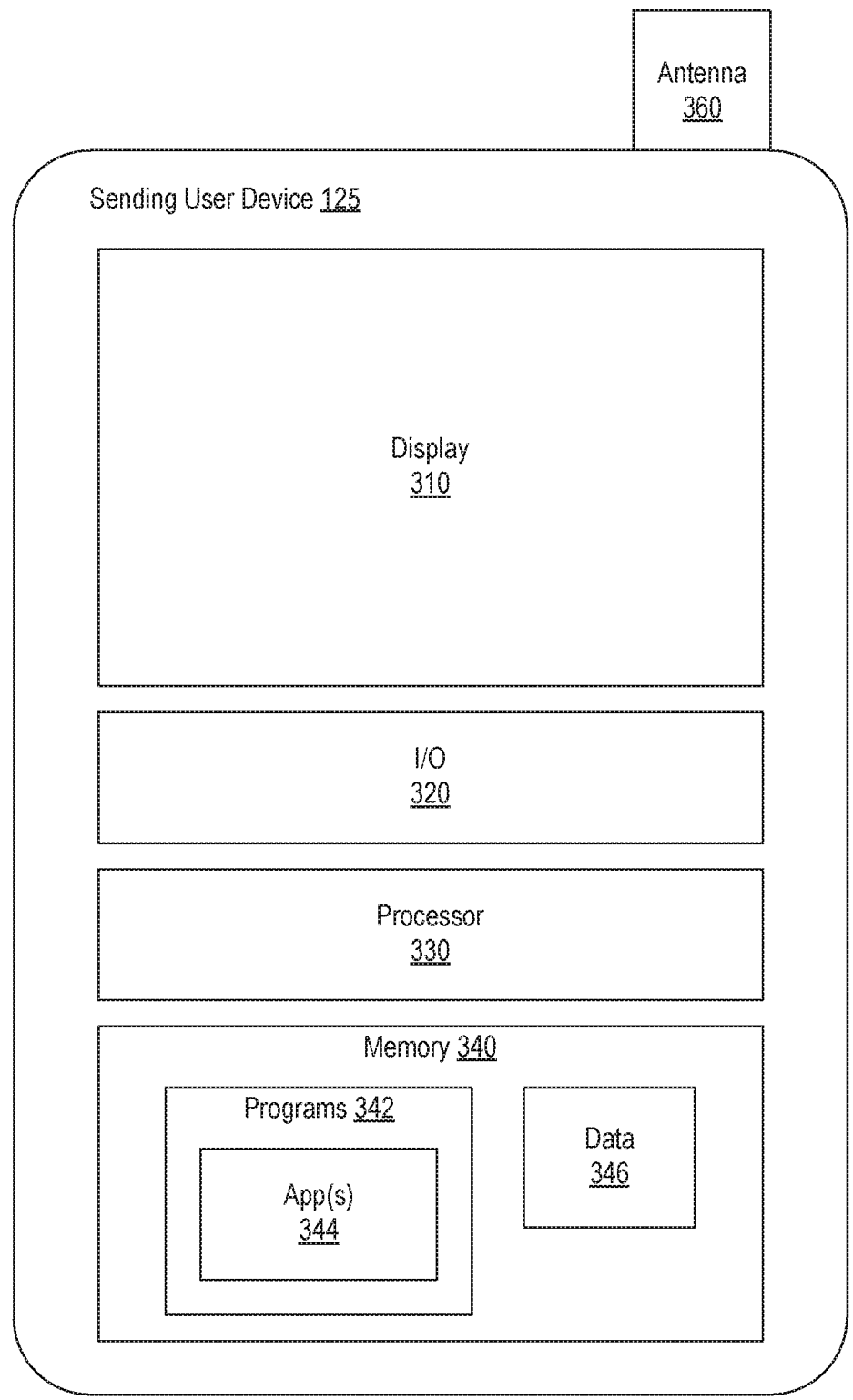
FIG. 3 depicts an example of a sending user device, consistent with embodiments of the present disclosure.

FIG. 3 shows a diagram of an exemplary sending user device 120, consistent with disclosed embodiments. As shown, sending user device 120 may include display 310, I/O device(s) 320, processor 330, memory 340 having stored thereon data 346 and one or more programs 342, such as app(s) 344 and antenna 360.

Display 310 may include one or more devices for displaying information, including but not limited to, liquid crystal displays (LCD), light emitting diode (LED) screens, organic light emitting diode (OLED) screens, and other known display devices.

I/O devices 320 may include one or more devices that allow mobile device 120 to send and receive information. I/O devices 320 may include, for example, a pointing device, keyboard, buttons, switches, and/or a touchscreen panel. I/O devices 320 may also include one or more communication modules (not shown) for sending and receiving information via antenna 360 from other components in system 100 by, for example, establishing wired or wireless connectivity between mobile device 120 to local network 110, network 150, or by establishing direct wired or wireless connections between sending user device 120 and other components of system 100. Direct connections may include, for example, Bluetooth™, Bluetooth LE™, WiFi, near field communications (NFC), or other known communication methods which provide a medium for transmitting data between separate devices.

Processor(s) 330 may be one or more known computing devices, such as those described with respect to processor 220 in FIG. 2.

Memory 340 may be a volatile or non-volatile, magnetic, semiconductor, tape, optical, removable, non-removable, or other type of storage device or tangible (i.e., non-transitory) computer-readable medium such as those described with respect to memory 250 in FIG. 2.

Figure 4:
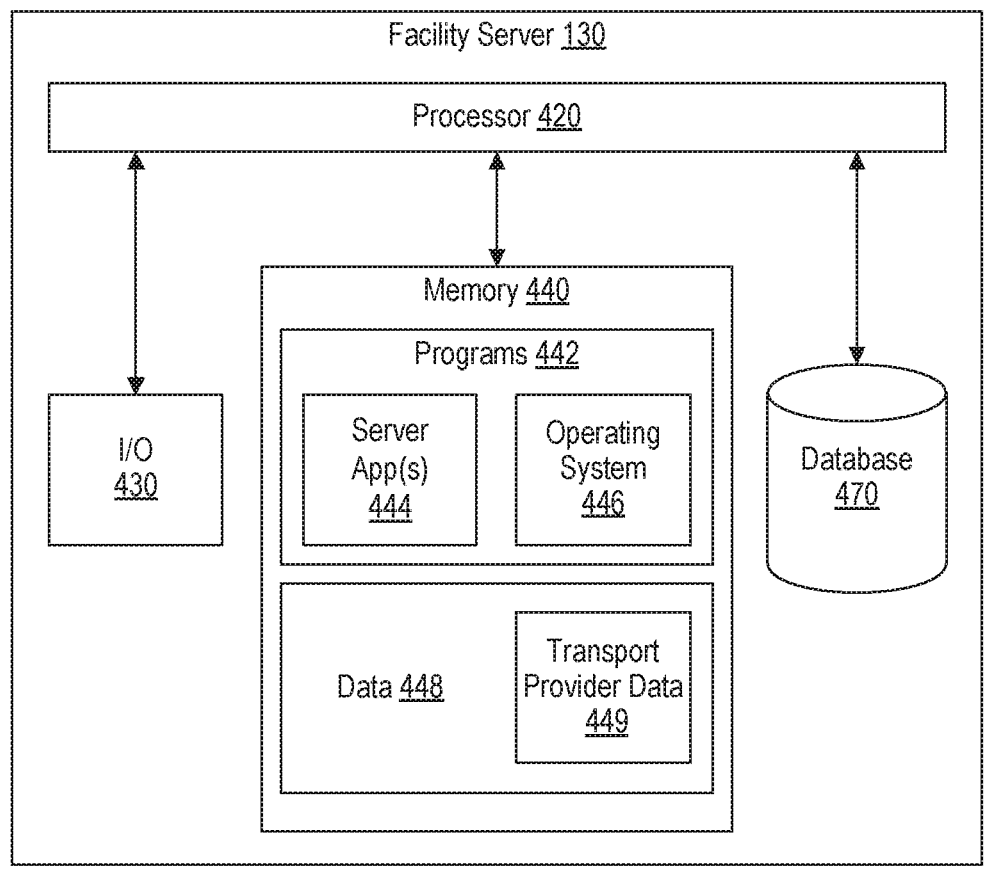
FIG. 4 depicts an example of a facility server, consistent with embodiments of the present disclosure.

FIG. 4 shows a diagram of an exemplary facility server 130, consistent with disclosed embodiments. In some embodiments, facility server 130 may be a local server within facility system 102. In such embodiments, facility server 130 may include one or more distributed computer systems capable of performing distributed computing functions, cloud computing services and functions, and interface-related functions consistent with disclosed embodiments. In some embodiments, facility server 130 may operate in conjunction with network server 130. In other embodiments, network server 160 may operate alone, and facility server 130 may be replaced by a network connection to network 150 and/or local network 110. In such embodiments, network server 160 may perform all functions associated with the disclosed methods. In other embodiments, facility server 130 may operate alone, without network server 160. In such embodiments, facility system 102 may operate as a stand-alone system, in which facility server 130 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

In some embodiments, facility server 130 may connect to multiple facilities located in different geographical locations. In such embodiments, facility server 160 may collect data from multiple facilities to evaluate performance times in different facilities, improve the accuracy of expected completion times for different types of tasks using one or more statistical/data regression algorithms, and predict future utilization of one or more of the facilities.

As shown in FIG. 4, facility server 130 may include one or more processor(s) 420, input/output ("I/O") devices 430, memory 440 storing programs 442 (including, for example, server app(s) 444 and operating system 446) and data 448 (including employee data 449), and a database 470. Facility server 130 may be a single server or may be configured as a distributed computer system including multiple servers or computers that interoperate to perform one or more of the processes and functionalities associated with the disclosed embodiments.

Processor(s) 420 may be one or more known computing devices, such as those described with respect to processor 220 in FIG. 2.

In some embodiments, facility server 130 may also include one or more I/O devices 430 including interfaces for receiving signals or input from devices and providing signals or output to one or more devices that allow data to be received and/or transmitted by network server 160. For example, facility server 130 may include interface components, which may provide interfaces to one or more input devices, such as one or more keyboards, mouse devices, and the like, that enable facility server 130 to receive input from one or more sending user 125 that is associated with facility system 102.

In some embodiments, facility server 130 may include one or more storage devices configured to store information used by processor 420 (or other components) to perform certain functions related to the disclosed embodiments. In one example, facility server 130 may include memory 440 that includes instructions to enable processor 420 to execute one or more applications, such as server applications, an electronic transaction application, an account status application, network communication processes, and any other type of application or software known to be available on computer systems. Alternatively or additionally, the instructions, application programs, etc. may be stored in an internal database 470 or external database 180 (shown in FIG. 1) in communication with facility server 130, such as one or more database or memory accessible over network 150. Database 470 or other external storage may be a volatile or non-volatile, magnetic, semiconductor, tape, optical, removable, non-removable, or other type of storage device or tangible (i.e., non-transitory) computer-readable medium.

In one embodiment, facility server 130 may include memory 440 that includes instructions that, when executed by processor 420, perform one or more processes consistent with the functionalities disclosed herein. Methods, systems, and articles of manufacture consistent with disclosed embodiments are not limited to separate programs or computers configured to perform dedicated tasks. For example, facility server 130 may include memory 440 that may include one or more programs 442 to perform one or more functions of the disclosed embodiments. Moreover, processor 420 may execute one or more programs located remotely from system 100. For example, facility server 130 may access one or more remote programs, that, when executed, perform functions related to disclosed embodiments.

Programs 450 stored in memory 440 and executed by processor(s) 420 may include one or more server app(s) 452 and operating system 454. Server app(s) 452 may incorporate one or more apps configured to receive input of information related to patient transfer needs and requests such as a new transfer request that may be initiated by sending user 125, bids from transportation providers quoting their services as a response to a transfer request, real-time data regarding pending transfer requests, transport provider queries regarding future patient transportation environments, and facility utilization data that may relate to predicting patient discharge or transfer dates. Facility utilization data may include such as capacity of various units, census data, and staffing levels, tracking patient statuses such as receiving patient attributes, diagnoses, and conditions, receiving staff schedules and staff skills, receiving one or more hospital rules and legal restrictions, receiving treatment requirements, physicians' orders and regimens associated with patient diagnoses. In some embodiments, system 100 may digitally interface with a post-acute care facility, and system 100 may receive a schedule and workload information for the post-acute care facility. In such embodiments, server 100 may utilize received schedule and workload information for the post-acute care facility in accordance with techniques disclosed herein, to automatically identify a post-acute care facility for the patient. To automatically identify such a facility, disclosed embodiments may use a number of factors. For example, disclosed embodiments may monitor the capacity of post-acute care facilities to determine whether one has space to accommodate a patient, and if it has space, disclosed embodiments may further probe to receive data regarding staffing at the facility capable of accommodating a patient. Additionally, if a facility does not have capacity, disclosed embodiments may query whether the facility has any scheduled or expected discharges that may create additional capacity. For example, server 100 may query the schedule of a facility to determine whether one or more patients are scheduled to leave a give post-acute facility in the next 24 hours. Disclosed embodiments may further consider insurance compatibility, cost, and/or whether a service-line is needed when identifying facilities. In such embodiments, a centralized system may handle the receipt of schedule and workflow information from an external facility, compare received information to medical record information indicating the medical needs of the patient, and patient schedule information, to automatically select and schedule post-acute care for the patient. For example, in some embodiments, a patient may provide access to an electronic schedule associated with the patient, such as a schedule stored on an electronic device of the patient. System 100 may compare a schedule retrieved from the patient to schedule and availability information associated with the transportation services and associated with the post-acute care medical facility.

Server app(s) 452 may also incorporate one or more apps configured to analyzing received data using one or more rule sets, computer models, or other processing logic, generating data associated with one or more graphical user interfaces, generating one or more communications and/or commands to other computer systems or devices such as sending user device 120, and updating the graphical user interfaces in real-time based on new data or changes in the analysis results.

In some embodiments, memory 440 may store data 448 including data associated with patients, staff, tasks, transfer requests, transportation quotes, transport providers, real-time transfer data, completed transfers, and graphical user interface generation algorithms, historical data, data derived from historical data such as trends, patterns, and correlative relationships. For example, data 448 may include one or more entries including transport provider data 449 (e.g., name, address, historical trip data, quality ratings), employee data (e.g., identification of staff, their skill sets, their schedules and availability, staff assignment history), patient medical records, patient assignment history, data associated with patient conditions, data associated with patient treatment plans, patient bed assignments, bed availability, bed locations, bed attributes, hospital rules, established hospital procedures, calculated patient itineraries associated with patient conditions and diagnoses, and legal restrictions and regulations. Data 448 may also include the current location of the patient, the status of each of the patient physician orders (e.g., lab orders, radiology orders), bed assignment priorities, milestones (e.g., discharge and transfer milestones), transport request status, patient hand-off during shift change, continuity of care data for resource assignments, custom patient attributes, and the real-time statuses of delays or complications in hospital departments and units. In some embodiments, system 100 may request and receive schedule information for a patient, in order to automatically schedule post-acute care and transportation to the post-acute care facility in accordance with techniques disclosed herein.

In some embodiments, data 448 is stored in database 470, memory 440, memory 250, memory 340, database 180, and any combination thereof.

In some embodiments, memory 440 and database 470 may include one or more memory devices that store data and instructions used to perform one or more features of the disclosed embodiments. Memory 440 and database 470 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Network server 160 may communicate with one or more remote memory devices (e.g., third-party server 170 and/or database 180) through network 150 or a different network (not shown). The remote memory devices may be configured to store information and may be accessed and/or managed by network server 160. By way of example only, the remote memory devices may be document management systems, Microsoft SQL database, SharePoint databases, Oracle™ databases, Sybase™ databases, or other relational databases. Systems and methods consistent with disclosed embodiments, however, are not limited to separate databases or even to the use of a database.

Figure 5:
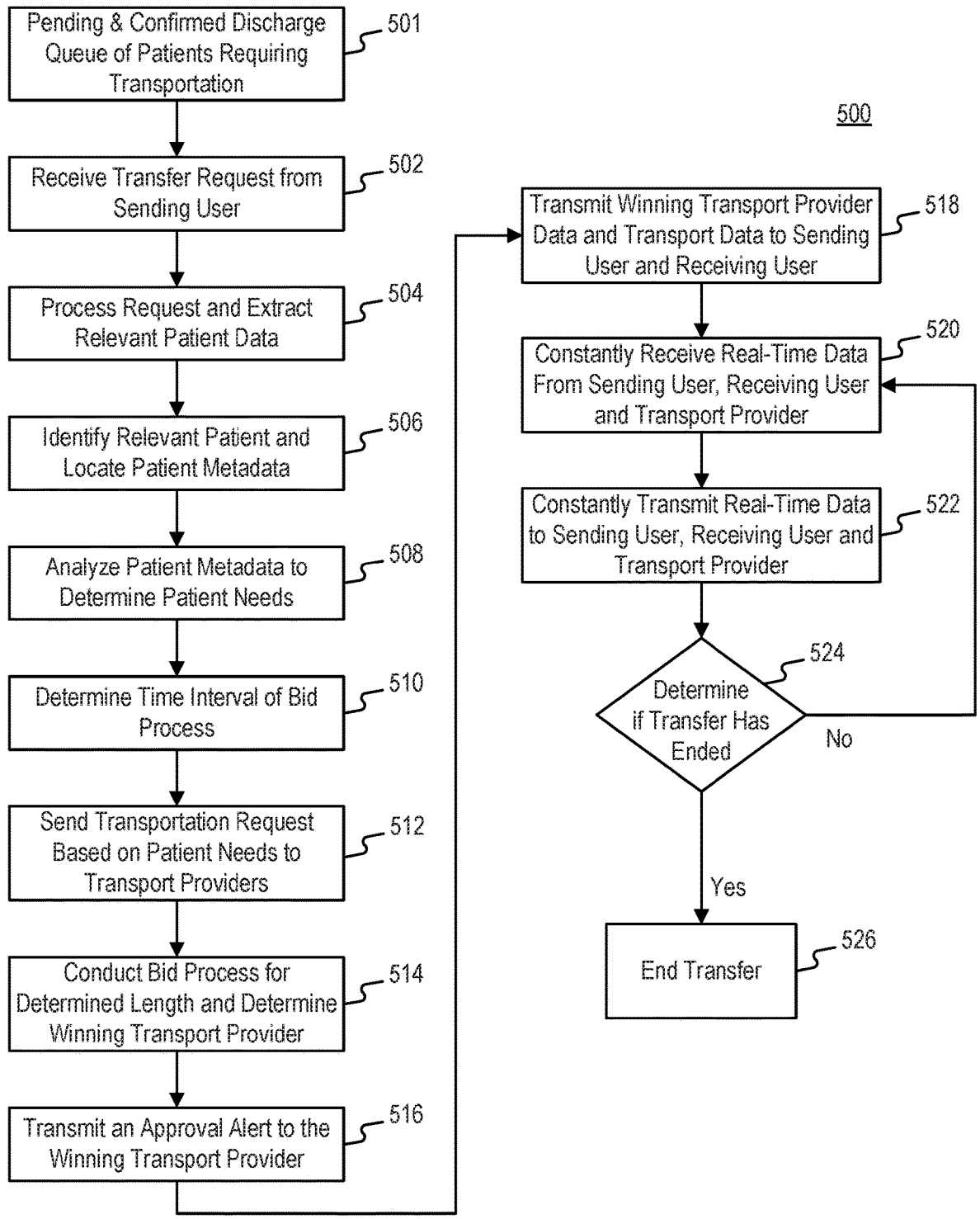
FIG. 5 depicts a flowchart of an exemplary process for requesting and monitoring optimal patient transport, consistent with embodiments of the present disclosure.

FIG. 5 is a flowchart for requesting and monitoring optimal patient transport, consistent with embodiments of the present disclosure. As shown, process 500 may include a series of steps including, for example, receiving and/or monitoring a queue of pending and confirmed discharge patients that need transportation in step 501. For example, process 500 may receive an indication that patient "John Doe" will discharge in 12 hours and has requested transportation. Process 500 may continue with receiving a transfer request from a sending user (e.g., a hospital where the patient is located) (step 502), processing the transfer request to extract relevant patient data (step 504), identifying the patient in need of a transfer and locating identified patient's metadata (step 506), analyzing patient metadata to determine patient needs (step 508), determining a length of a bid process based on determined patient needs (step 510), sending transportation request based on patient needs to transport providers (step 512), conducting the bid process for determined length and determining winning transport provider (step 514), transmitting an approval alert to the winning transport provider (step 516), transmitting the winning bid provider data and transport data to sending user and receiving user (step 518), constantly receiving and transmitting real-time data from and to the sending user, receiving user, and transport provider (step 520 and step 522), and ending the transfer if it is determined that the transfer has ended (step 524 and 526). Process 500 provides medical care facilities and medical care systems, such as hospitals and hospital systems, and/or managed care organizations with a mechanism to greatly enhance their capacity management system and patient flow procedures, allowing optimal utilization of valuable facility space. It also helps these facilities and systems obtain real-time data on any pending transfers ensuring complete visibility, which permits the medical care facilities and medical care systems to take appropriate contingency or emergency actions in a timely and efficient manner. Process 500 is described herein as being performed primarily by facility server 130. In some embodiments, however, one or more computerized devices of system 100 may perform steps of process 500, as well as any other process disclosed herein. In some embodiments, multiple devices may perform steps of the methods disclosed herein in a distributed computing fashion.

While FIG. 5 illustrates an exemplary process for selecting and monitoring a transportation request, in some embodiments certain steps of process 500 may be implemented to select a post-acute care facility.

In some embodiments, system 100 may execute a computerized platform for a marketplace for processing received requests from a medical facility such as a hospital, to generate one or more bid requests from one or more external post-acute care medical facilities such as a skilled nurse facility (SNF) or a long term care (LTC). In some embodiments, the one or more external post-acute care medical facilities may be previously-registered with system 100, and in other embodiments system 100 may identify unregistered post-acute care medical facilities, and generate and transmit electronic communications to the identified post-acute care medical facilities. In some embodiments, bid requests may include identification information (anonymous or personal) for a list of discharge patients needing post-acute care after discharge from the hospital. In some embodiments, a software application for generating transfer requests running on system 100 may automatically generate and transmit the bid request(s) to post-acute care medical facilities in response to a determination that the patient is estimated to be discharged within a predetermined amount of time, and that the patient's medical record indicates the need for post-acute care. In some embodiments, system 100 may receive one or more bid messages from the post-acute care medical facilities. System 100 may automatically process received bids in accordance with techniques disclosed herein. Thereafter, system 100 may select a post-acute medical facility, and generate one or more requests for transportation to the selected post-acute medical facility in accordance with techniques disclosed herein. In some embodiments, system 100 may receive acknowledgment and acceptance messages from the selected post-acute medical facility.

Step 502 may comprise the facility server 130 receiving a transfer request from a sending user 125, such as, but not limited to, a medical care facility or medical care system. In some embodiments, the transfer request may include patient identifiers, patient location, desired destination, patient discharge time, any requirements specific to the transfer itself, and other pertinent information related to the transfer (e.g., required equipment, patient age, patient height, patient weight, whether the patient is ambulatory, whether the patient requires oxygen, whether the patient has a co-passenger guardian, whether the patient requires skilled nursing during transport, and the like). For example, if a patient has a required time pick-up or drop-off time, then the transfer request would include such data. In other embodiments, the pick-up and drop-off times may not be a strict requirement, and instead, the sending user 125 may only list the discharge time indicating what time the patient is available to be picked up. Some other embodiments may allow sending user 125 to write in specific notes that would be incorporated into the transfer request. Patient identifiers include, but are not limited to, patient name, patient identification number, social security number, or some other identifier.

In step 504, facility server 130 may process the received transfer request and extracts relevant patient data from the storage. In some embodiments, the facility server 130 may have stored patient data relevant to that patient's transfer. In some embodiments, current patient data may include any information or combination of different types of information reflecting the current status of a patient of a hospital or healthcare system.

In step 506, facility server 130 may analyze the extracted data to identify the relevant patient, and locate patient metadata from storage. For example, the facility server 130 may take the inputted patient identifier(s) and extract from its storage information that can pinpoint the exact patient that the transfer request is for and access the specific stored patient metadata for that patient. Patient metadata include medical conditions, diagnosis, level of service needed, other medical information, and other data stored on the facility server 130, as described in FIG. 4.

In Step 508, the patient's metadata may be analyzed by the facility server 130 to determine patient needs. For example, the facility server 130 may perform this analysis and determine that the patient requires specialized equipment, such as a wheelchair, or other resources in order to be adequately and safely transferred. A variety of patient needs can be determined based on the patient metadata analysis, and such needs will be used to acquire adequate transportation to properly complete the patient transfer. Patient needs may include required drop-off times at receiving facility, basic or advanced life support equipment, specific medicine, medicinal or food allergies, isolation, diagnosis, psychological needs, wheelchair equipment, specialized patient transfer boards, pivot discs, ventilators, and other restrictions or equipment.

In Step 510, the facility server 130 will determine a time interval for a bid process based on the transfer request data, patient needs data or other data stored in the facility server 130, or a combination of any of the three sets of data. For example, if the transfer request has specific restrictions on when the patient must be picked up, then the bid process length would be calculated based on such data to ensure a transfer meets the restriction and still allows the optimal time to attract competitive transport bids. In some embodiments, the bid process time interval would be shortened to the time it takes for the first bid to come in. For example, if the sending user 125 makes a transfer request for immediate pick-up, then the facility server 130 would set the bid process time interval to the time it takes to receive a transportation bid that meets all other requirements.

In Step 512, a transportation request is broadcast to transport providers detailing the determined patient needs and other requirements for the specific request. The transfer request may incorporate the determined patient needs data, the initial data received from the transfer request, any data extracted from processing the transfer request and any other data stored in the facility server 130. In Step 514, the facility server 130 will conduct the bid process for the time interval determined in Step 510 and, after closing the bid process, determine a winning transport provider. For example, once the transportation request is sent out to the transport providers, then the bid process may be conducted for a set amount of time depending on the patient and sending user needs. The facility server 130 will continuously compare incoming bids to determine which bid is better based on numerous factors. These factors may include, but are not limited to, costs for sending user, costs for patient, resource optimization (e.g. making patient beds available sooner for other patients), cost for boarding the patient until the following day (e.g., whether the cost of transport will decrease the following day, making boarding another day and later transport less costly than immediate transport), transfer conditions provided for patient, historical transport provider data, and transport provider quality rating.

Figure 6:
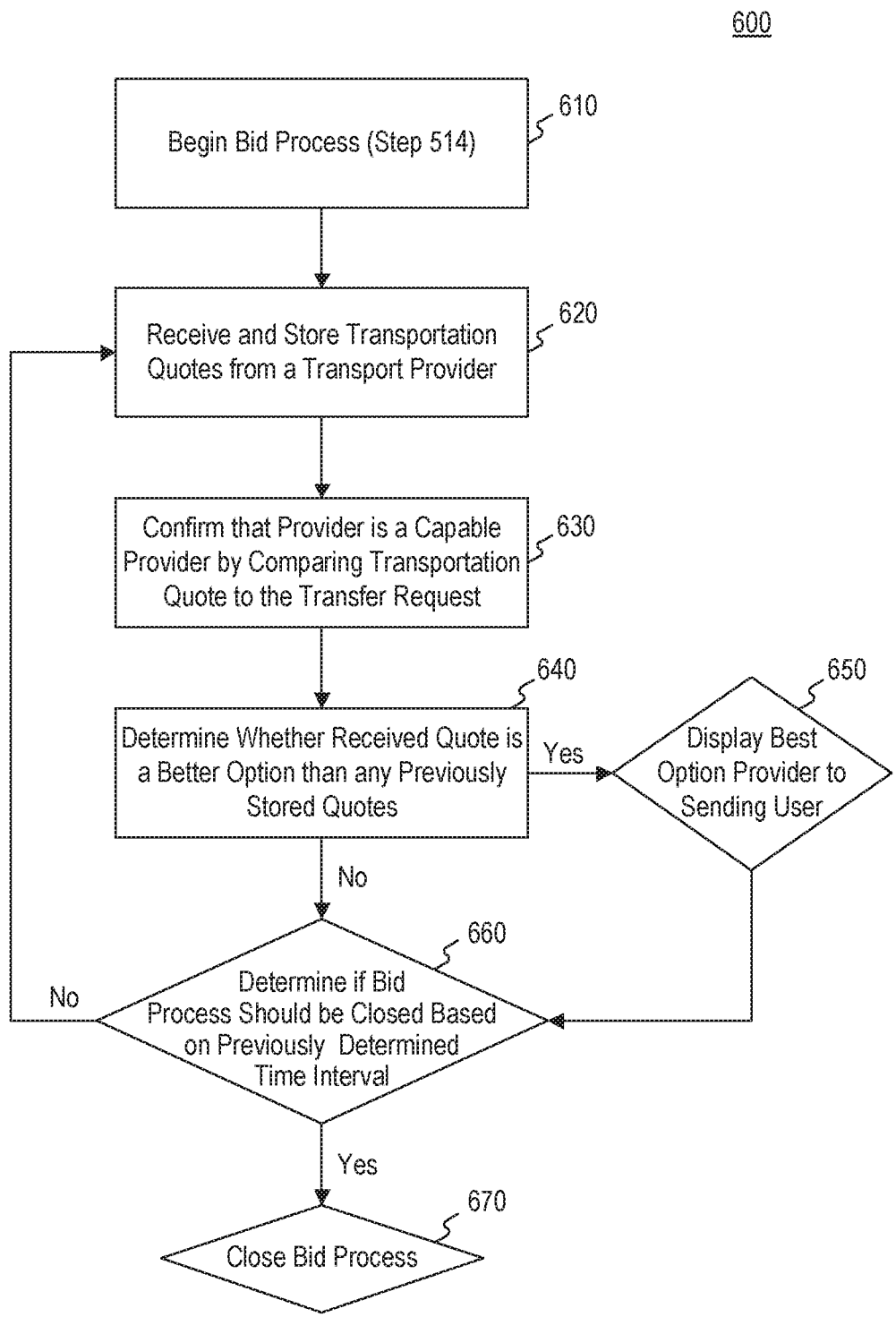
FIG. 6 depicts a flowchart of an exemplary process for conducting a bid process to obtain transportation quotes from transport providers, consistent with embodiments of the present disclosure.

FIG. 6 expands on the bid process discussed in Step 514. FIG. 6 depicts a flowchart describing the bid process 600 that allows transport providers to submit quotes to acquire a transfer request. FIG. 6 expands on the detailed description from FIG. 5. In Step 610, the bid process begins as it did in Step 514 in FIG. 5. In Step 620, the facility server 130 receives a transportation quote from a transport provider and stores the quote in storage. For example, a transport provider may receive a transfer request from sending user 125, and, in response, submit a quote accepting the requirements of the transfer request and detailing any other pertinent information (e.g., cost, vehicle type, etc.). In Step 630, the facility server 130 will compare the transportation quote to the transfer request to ensure that the quote meets the requirements and that the transport provider is capable of performing the request. For example, if the transfer request lists a certain type of vehicle to accommodate a patient's need, such as a wheelchair, then the facility server 130 will compare the data provided in the transportation quote to ensure that an appropriate vehicle is being provided. In some embodiments, the facility server 130 may not need to perform this step.

In Step 640, the facility server 130 may determine whether the received quote is a better option than any previously stored quotes based on a variety of factors. The factors may include, but are not limited to, cost to sending user 125, cost to patient, insurance provider compatibility, resource optimization, and transport provider quality rating (e.g., qualitative rating, such as user feedback scores, and/or quantitative rating, such as percentage of on-time arrivals, on-time departures, and response time). For example, with regards to resource optimization, the facility server 130 may compile data, such as hospital conditions, scheduling information and updates, resource availability (e.g., patient beds) from various sources, such as computer terminal 140 and other integrated systems, to determine the impact of choosing one provider over another, and optimizing the transfer by selecting the provider that allows the hospital to optimally use their resources. In some embodiments, this step may involve using the data stored in facility server 130, as described in FIG. 4. In Step 650, if the received transportation quote is better than any previously stored transportation quotes, then the facility server 130 will display information corresponding to the better transportation quote on the sending user device 120. If a previously stored transportation quote is a better option than the received transportation quote, then the facility server 130 will determine if the bid process should be closed based on the time interval determined in FIG. 5 (Step 660), as described in FIG. 5. If the determined time interval has not been met, then the facility server 130 continues to receive transportation quotes from transport providers. However, if the determined time interval has been met, then the facility server 130 closes the bid process (Step 670).

In Step 516, the facility server 130 will transmit an approval alert to the winning transport provider notifying the transport provider that their bid is accepted. The transmission may include an interface showing the time the transport provider is expected to pick-up the patient from the sending user, the expected drop-off time at the receiving user, and any other information regarding specific restrictions or requirements for the transfer based on the transfer request and accepted transportation quote. In Step 518, the facility server 130 will also transmit winning bid provider data and transport data to the sending user 125 and receiving user 185. For example, once the winning bid provider is determined, then the sending user 125 may receive information including, but not limited to, contact information, insurance accepted by transport provider, type of vehicle, accompanying equipment, estimated time of pick up, and estimated time of drop off.

Figure 7:
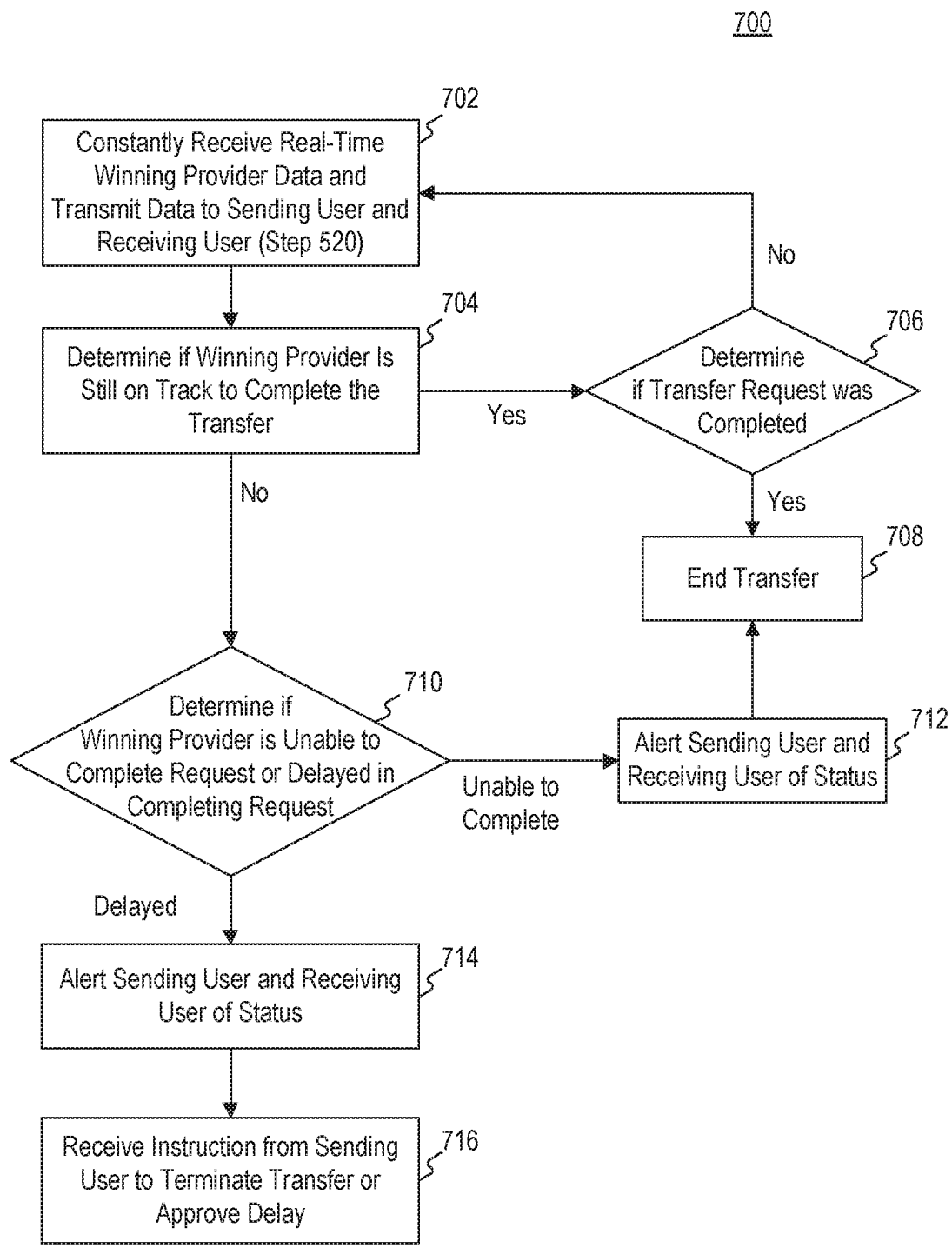
FIG. 7 depicts a flowchart of an exemplary process for real-time tracking of the patient transfer, consistent with embodiments of the present disclosure.

In Step 520, the facility server 130 may constantly receive real-time data from sending user 125, receiving user 185 and the winning transport provider. For example, facility server 130 may receive data every 10 minutes, every minute, every second, and/or every time new data is received or generated (e.g., when an update is provided by a terminal of the system). In some embodiments, this information may include, but is not limited to, transfer status, estimated time of arrival at sending user 125 location and receiving user 185 location, and patient building location. FIG. 7 depicts a flowchart describing the real-time process 700 of the patient transfer application. In Step 702, the facility server receives real-time data from the sending user 125, receiving user 185 and transport provider, as previously described in FIG. 5. In some examples, this data may include, but is not limited to, updated pick-up requirements at the sending user facility, availability conditions at the receiving user facility, updated estimated time of arrival at pick-up or drop-off location, or transport provider GPS location. In Step 704, the facility server 130 may determine if the winning provider is still on track to complete the transfer. In some embodiments, the facility server 130 may use GPS tracking to determine current transport provider location in relation to expected transport provider location, and, if the current transport provider location does not meet a relativity standard, then the facility server 130 may request a status update from the transport provider. In some examples, the expected transport provider location would incorporate the agreed upon pick-up time in the accepted transportation quote and global traffic data to determine the expected location of the transport provider at any given time. The facility server 130 may calculate the relativity standard by comparing the current transport provider location and expected transport provider location to determine if the difference between the two locations is greater than some predetermined threshold. If the transport provider is on track to complete the transfer, then, in Step 706, the facility server determines whether the transfer request is complete and ends the transfer if it is (Step 708). If the transfer is not complete, the facility server 130 constantly receives real time data to determine if the winning transport provider is on track to complete the transfer (Step 702 and 704).

In Step 710, if the winning transport provider is not on track to complete the transfer, then the facility server determines whether the transport provider is unable to complete the transfer request or is delayed in completing the transfer request. In some examples, the facility server 130 may send an alert requesting information from the transport provider regarding the transport provider's ability to complete the transfer request. If the transport provider responds to the alert indicating its inability to complete the request, then facility server 130 may alert the sending user and receiving user (Step 712) and end the transfer (Step 708). In other embodiments, if the transport provider responds to the alert indicating that it is only delayed in completing the request, then, in Step 714, the facility server 130 may alert the sending user and receiving user of the delayed status of the transport provider. In Step 716, the facility server 130 may allow the sending user 125 to terminate the transfer or approve the delay. Although not depicted in FIG. 7, process 700 may re-initiate the bidding process or follow-up with one or more runner-up bidders when a transfer is terminated. In certain embodiments, as the delay exceeds a predefined threshold, process 700 may contact one or more bidders that did not win in order to secure potential alternative transportation. For example, prior to sending user 125 terminating the transfer, process 700 may send a message to one or more bidders who did not win, querying whether they would be available to serve as transport should sending user 125 terminate an existing transfer. Should a bidder transmit an acceptance, process 700 may present the user with an option to "terminate existing transfer and use an alternate provider."

Referring back to FIG. 5, in Step 522, the facility server 130 may transmit any received real-time data to the sending user 125, receiving user 185, and the winning transport provider. In Step 524, the facility server will determine if the transfer has ended, and, if it has, it will end the transfer (Step 526), or, if the trip is still pending, then it will continue to constantly receive real-time data (Step 520) and transmit received data (Step 522).

Figure 8:
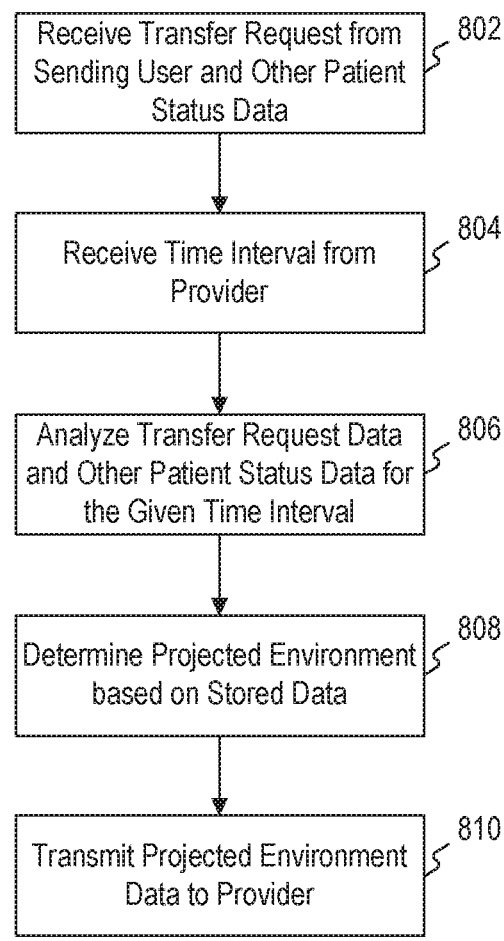
FIG. 8 depicts a flowchart of an exemplary process for projecting a patient transportation environment, consistent with embodiments of the present disclosure.

FIG. 8 depicts a flowchart of process 800 for calculating projected medical transport environments. Step 802 is similar to step 502 in FIG. 5 in that the facility server 130 receives a transfer request from sending user 125. In addition, facility server 130 may also receive other patient status data already stored in facility system 102. The data may be stored in the facility server 130 or at another location. The other patient status data may include, but is not limited to, number of patients at the facility, patient discharge times, patient condition, projected patient discharges, and pending patient discharges.

In Step 804, the facility server 130 may receive a time interval from a transport provider. For example, a transport provider may want to understand projected patient flow for the next day at a certain hospital or in a certain geographical location. In order to retrieve the information, the transport provider may request a projected patient transfer environment for a certain time period. In some embodiments, the facility server 130 may obtain other patient status data from multiple facilities allowing facility server 130 to analyze data for broader geographical locations, rather than just specific facilities.

In Step 806, the facility server 130 may analyze the transfer request data and other patient status data for the given time interval. In some examples, the facility server 130 may analyze other patient status data and transfer request data to determine probabilities of a facility or location making patient transfer requests within the received time interval. For example, facility server 130 may analyze patient status data to determine pending or potential discharges based on patient conditions, diagnosis and other patient data. In Step 808, the facility server 130 may determine a projected patient flow environment based on the analysis Step 806. In some examples, the projected environment may be calculated based on the probabilities of potential future need for patient transfers. For example, based on the analysis in Step 806, facility server 130 may determine the various probabilities that a patient may be discharged within a set time period and that a patient may be discharged at a specific time. In Step 810, the facility server 130 may transmit the projected environment data to the provider. In some examples, the data transmitted may be depicted in a map showing a range of probabilities for a certain location for the time interval provided.

Figure 9:
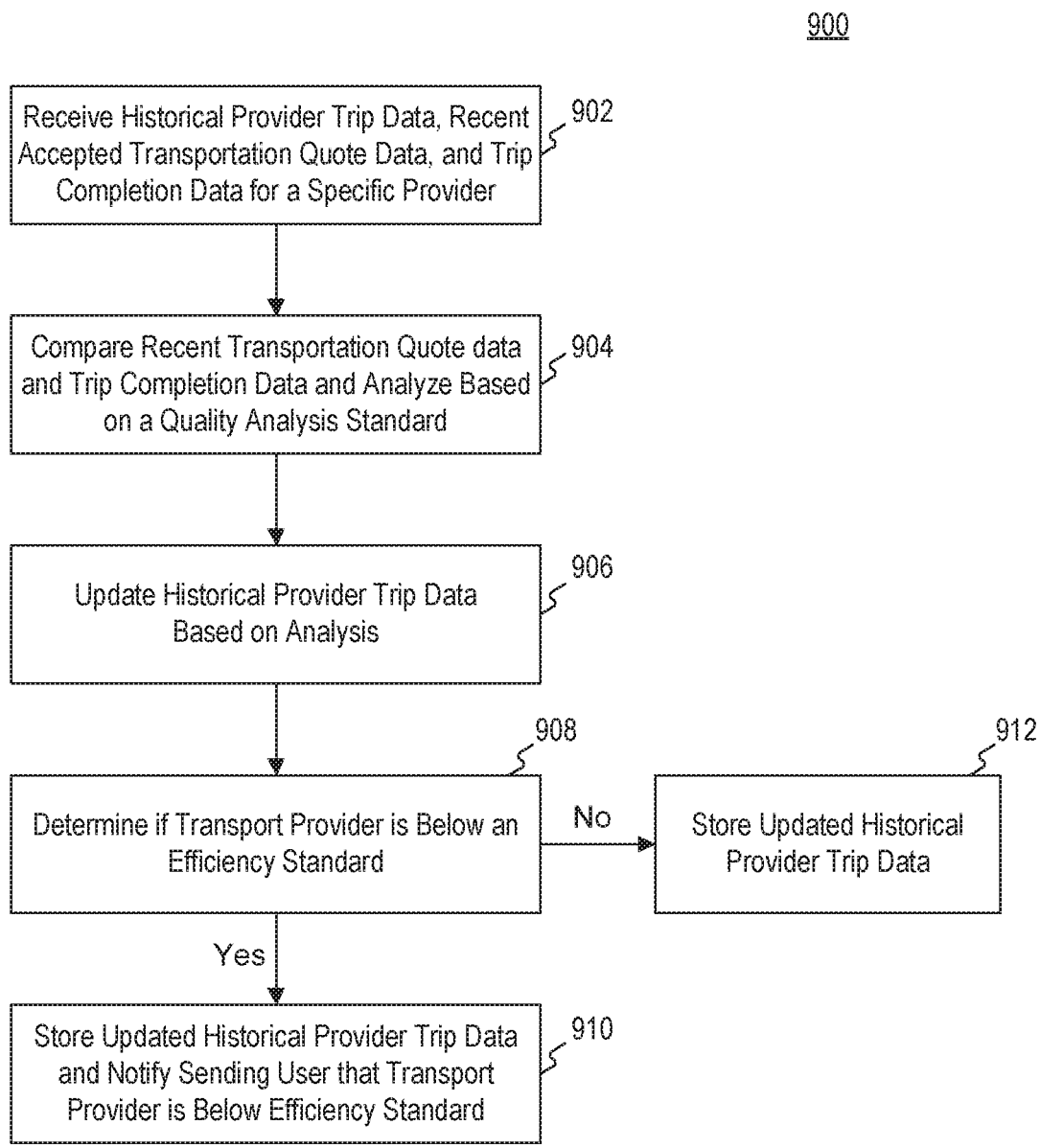
FIG. 9 depicts a flowchart of an exemplary process for processing a transport provider's quality rating based on recent trip data and historical trip data, consistent with embodiments of the present disclosure.

FIG. 9 depicts a flowchart of process 900 for determining the quality of service a transport provider offers based on patient transfers completed. In Step 902, the facility server 130 receives historical provider trip data, recent accepted transportation quotes data, and trip completion data for a specific provider after that provider completes a patient transfer. The historical provider data may include, but is not limited to, time and quality efficiency information, number of cancellations, patient customer rating, and previous quality rating. Recent accepted transportation quote data may refer to information acquired during the transfer request process, as described in FIG. 5. Trip completion data may correspond with actual data of the most recent trip the provider completed.

In Step 904, the facility server 130 analyzes recent accepted transportation quote data and the trip completion data to decipher if any discrepancies exist. For example, if the agreed upon transportation quote required the provider to pick-up the patient at a certain time, but the trip completion data showed that the provider was delayed, then this discrepancy would be discovered by the facility server 130. If a discrepancy exists, the facility server 130 may quantify the discrepancy based on a quality analysis standard. In some examples, the quality analysis standard may be based on a point-based system that correlates discrepancies to certain point values. In other instances, the quality analysis standard may involve numerous factors including predetermined categories evaluated at different weights based on the facility's preference. For example, if the facility greatly valued a provider being on time to pick-up a patient, then the discrepancy between the actual time a patient is picked-up and the time the patient was supposed to be picked up may be weighted greater than other factors that help determine the quality analysis standard. Some factors that may help determine the quality analysis standard may include, but not limited to, quantity difference in agreed upon pick-up or drop-off time and actual pick-up or drop-off time, percent difference in agreed upon pick-up or drop-off time and actual pick-up or drop-off time, difference in cost agreed upon and actual cost, and difference in equipment agreed upon and equipment provided. If no discrepancies exist, the facility server 130 may quantify the successful trip against the quality analysis standard. In some examples, the analysis based on the quality analysis standard may correspond to a transport provider rating.

In Step 906, the facility server 130 may update the historical provider trip data to incorporate the analysis in Step 904. In some examples, the facility server 130 will weigh the analysis of the recent trip conducted in Step 904 against previous analysis of previously completed trip. For example, if the transport provider received a transport provider rating for a recent trip from a patient and/or caregiver, then the facility server will weigh this transport provider rating against all previously stored transport provider ratings within the historical provider trip data. In some embodiments, the recent trip may weigh equally against all previously completed trips. In Step 908, after the historical provider trip data is updated, the facility server 130 will determine if transport provider is below an efficiency standard. In some examples, the efficiency standard may be a threshold transport provider rating, and, if the transport provider rating falls below that threshold, then the transport provider is below an efficiency standard. If the facility server 130 determines that the transport provider is below an efficiency standard, then the facility server 130 will notify the sending user of this occurrence and store the updated historical provider trip data (Step 910). If the transport provider is not below an efficiency standard, then the facility server 130 may store the updated historical provider data.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone. Further, while the embodiments described related to patients in a facility, some embodiments may relate to utilization with respect to staff, members of the public, guests, contactors, or equipment.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

What is claimed is:

1. A computerized system for requesting and monitoring optimal patient transport, the system comprising:
   at least one processor in communication with a communications network; and
   a storage medium comprising instructions that, when executed, configure the at least one processor to:
   receive, from a computer terminal within a facility, transfer request data from an initial user for a patient, wherein the transfer request data comprises information corresponding to a pick-up time for a transport for the patient;
   identify, from the transfer request data, the patient and patient data corresponding to the identified patient, wherein to identify the patient data comprises identifying patient transport requirements by analyzing, using a facility server, the patient data;
   transmit a transfer request to one or more transport user devices corresponding to one or more transport providers through a bid process that is set for a specific time interval, wherein the specific time interval is based, at least in part, upon the pick-up time and the patient transport requirements, wherein the transfer request is displayed in a graphical user interface on the one or more transport user devices and wherein the graphical user interface allows for user interaction by the one or more transport providers;
   receive and store one or more transportation quotes provided within the graphical user interface from one or more of the one or more transport providers;
   analyze the one or more transportation quotes received against previously stored transportation quotes, wherein to analyze comprises comparing the one or more transportation quotes received with the previously stored transportation quotes and identifying, based upon one or more factors, one of the one or more transportation quotes and the previously stored transportation quotes corresponding to an optimization of resources of the facility;
   determine a winning transport provider and pending transport data based on the one or more transportation quotes received, wherein to determine comprises selecting, responsive to the specific time interval expiring, a transport provider corresponding to the one or more transportation quotes and the previously stored transportation quotes identified as corresponding to an optimization of resources of the facility;
   generate, based on the pending transport data, instructions to display a user interface at the transport user device of the winning transport provider depicting a first representation of a pending transport at a first time;
   receive real-time and historical data associated with a facility and the pending transport; and
   generate, based on the real-time and historical data, instructions to display a user interface within a patient transportation application of the computer terminal depicting a second representation of progress of the pending transport at a second time.

2. The computerized system of claim 1, wherein:
   the first time is a time prior to the start of the pending transport; and
   the second representation comprises a projected pending transport at the second time based on the real-time and historical data.

3. The computerized system of claim 1, wherein determining relevant patient data is based on analyzing previously stored patient data.

4. The computerized system of claim 3, wherein the at least one processor is further configured to extract patient requirements based on the previously stored patient data.

5. The computerized system of claim 1, wherein the at least one processor is further configured to determine the time interval for the bid process based on the relevant patient data.

6. The computerized system of claim 1, wherein the identifying comprises identifying the received transportation quote as corresponding to the optimization of resources of the facility as compared with other of the one or more transportation quotes and the previously stored transportation quotes.

7. The computerized system of claim 6, wherein, before and up until the winning transport provider is determined, the at least one processor is further configured to generate instructions to display a user interface depicting a representation of the received transportation quote.

8. The computerized system of claim 5, wherein, the at least one processor is further configured to close the bid process after the determined time interval has lapsed.

9. The computerized system of claim 5, wherein, the at least one processor is further configured to generate instructions to display a projected patient environment map based on patient status data, wherein the patient status data comprises transfer request data for all patients or potential patient data.

10. A computerized method for requesting and monitoring optimal patient transport, the method comprising:
    receiving, from a computer terminal within a facility and by at least one processor in communication with a communications network, transfer request data from an initial user for a transferee, wherein the transfer request data comprises information corresponding to a pick-up time for a transport for the transferee;
    identifying, from the transfer request data, the transferee and transferee data corresponding to the identified transferee, wherein the identifying the transferee data comprises identifying transferee transport requirements by analyzing, using a facility server, the transferee data;
    transmitting a transfer request to one or more transport user devices corresponding to one or more transport providers through a bid process that is set for a specific time interval, wherein the specific time interval is based, at least in part, upon the pick-up time and the transferee transport requirements, wherein the transfer request is displayed in a graphical user interface on the one or more transport user devices and wherein the graphical user interface allows for user interaction by the one or more transport providers;
    receiving and storing one or more transportation quotes provided within the graphical user interface from one or more of the one or more transport providers;

analyzing the one or more transportation quotes received against previously stored transportation quotes, wherein the analyzing comprises comparing the one or more transportation quotes received with the previously stored transportation quotes and identifying, based upon one or more factors, one of the one or more transportation quotes and the previously stored transportation quotes corresponding to an optimization of resources of the facility;

determining a winning transport provider and pending transport data based on the one or more transportation quotes received, wherein the determining comprises selecting, responsive to the specific time interval expiring, a transport provider corresponding to the one or more transportation quotes and the previously stored transportation quotes identified as corresponding to an optimization of resources of the facility;

generating, based on the pending transport data, instructions to display a user interface at the transport user device of the winning transport provider depicting a first representation of a pending transport at a first time;

receiving real-time and historical data associated with a facility and the pending transport; and generating, based on the real-time and historical data, instructions to display a user interface within a patient transportation application of the computer terminal depicting a second representation of progress of the pending transport at a second time.

11. The computerized method of claim 10, wherein:
the first time is a time prior to the start of the pending transport; and
the second representation comprises a projected pending transport at the second time based on the real-time and historical data.

12. The computerized method of claim 10, wherein determining relevant transferee data is based on analyzing previously stored patient data.

13. The computerized method of claim 12, further comprising extracting transferee requirements based on the previously stored transferee data.

14. The computerized method of claim 10, further comprising determining the time interval for the bid process based on the relevant transferee data.

15. The computerized method of claim 10, wherein the identifying comprises identifying the received transportation quote as corresponding to the optimization of resources of the facility as compared with other of the one or more transportation quotes and the previously stored transportation quotes.

16. The computerized method of claim 15, further comprising, before and up until the winning transport provider is determined, generating instructions to display a user interface depicting a representation of the received transportation quote.

17. The computerized method of claim 14, further comprising closing the bid process after the determined time interval has lapsed.

18. The computerized method of claim 14, further comprising generating instructions to display a projected transferee environment based on transferee status data, wherein the transferee status data comprises transfer request data for all transferees or potential transferee data.

19. A non-transitory computer-readable medium storing instructions which, when executed, cause one or more processor to perform a method for requesting and monitoring optimal patient transport, comprising:

receiving, from a computer terminal within a facility and by at least one processor in communication with a communications network, transfer request data from an initial user for a transferee, wherein the transfer request data comprises information corresponding to a pick-up time for a transport for the transferee;

identifying, from the transfer request data, the transferee and transferee data corresponding to the identified transferee, wherein the identifying the transferee data comprises identifying transferee transport requirements by analyzing, using a facility server, the transferee data;

transmitting a transfer request to one or more transport user devices corresponding to one or more transport providers through a bid process that is set for a specific time interval, wherein the specific time interval is based, at least in part, upon the pick-up time and the transferee transport requirements, wherein the transfer request is displayed in a graphical user interface on the one or more transport user devices and wherein the graphical user interface allows for user interaction by the one or more transport providers;

receiving and storing one or more transportation quotes provided within the graphical user interface from one or more of the one or more transport providers;

analyzing the one or more transportation quotes received against previously stored transportation quotes, wherein the analyzing comprises comparing the one or more transportation quotes received with the previously stored transportation quotes and identifying, based upon one or more factors, one of the one or more transportation quotes and the previously stored transportation quotes corresponding to an optimization of resources of the facility;

determining a winning transport provider and pending transport data based on the one or more transportation quotes received, wherein the determining comprises selecting, responsive to the specific time interval expiring, a transport provider corresponding to the one or more transportation quotes and the previously stored transportation quotes identified as corresponding to an optimization of resources of the facility;

generating, based on the pending transport data, instructions to display a user interface at the transport user device of the winning transport provider depicting a first representation of a pending transport at a first time;

receiving real-time and historical data associated with a facility and the pending transport; and generating, based on the real-time and historical data, instructions to display a user interface within a patient transportation application of the computer terminal depicting a second representation of progress of the pending transport at a second time.

20. The non-transitory computer-readable medium of claim 19, wherein:
the first time is a time prior to the start of the pending transport; and
the second representation comprises a projected pending transport at the second time based on the real-time and historical data.

* * * * *